Figures 1A, 1B, 1C:
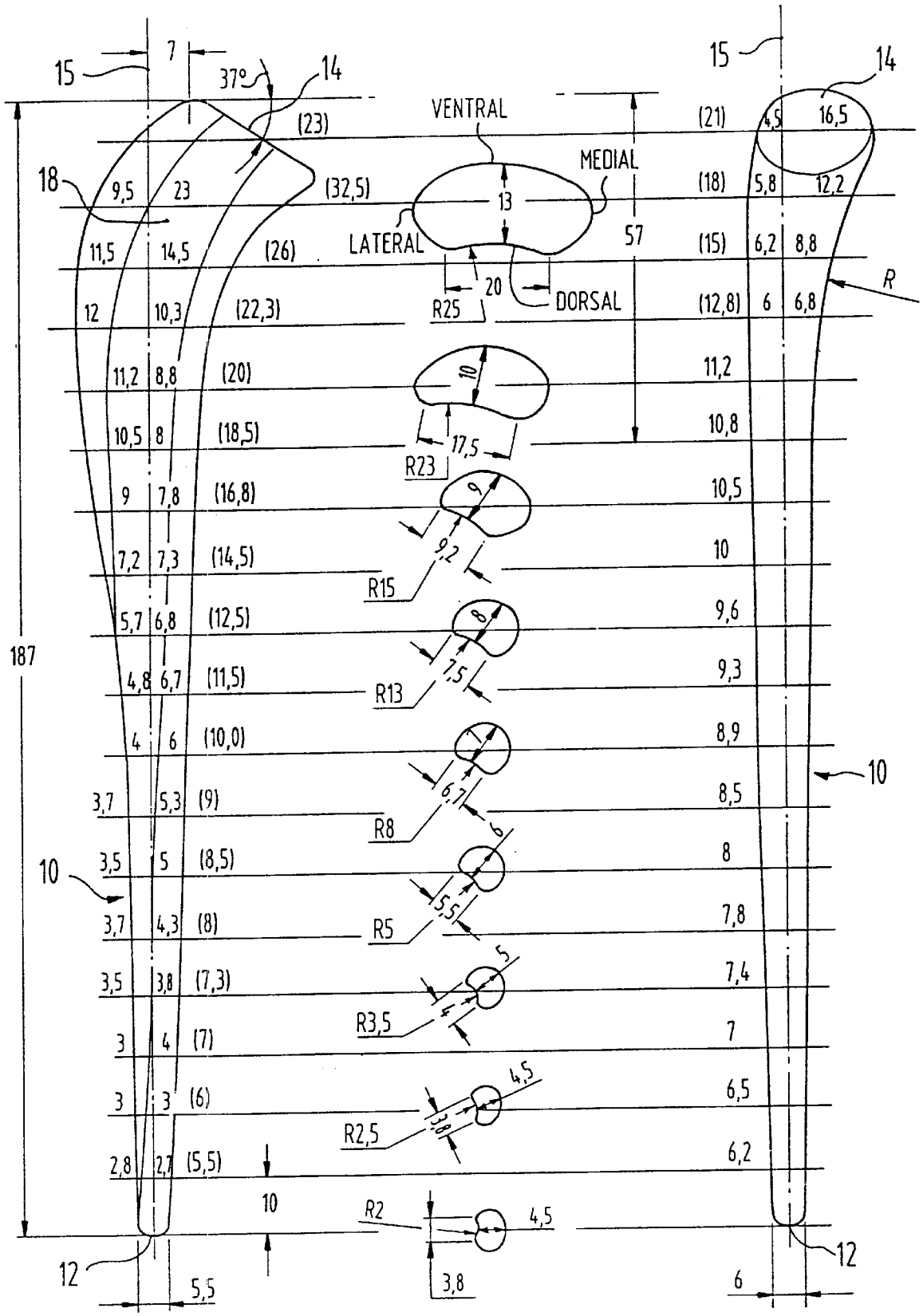

United States Patent [19]
Draenert

[11] Patent Number: 5,888,210
[45] Date of Patent: Mar. 30, 1999

[54] STEM OF A FEMORAL COMPONENT OF A HIP JOINT ENDOPROSTHESIS

[76] Inventor: Klaus Draenert, Gabriel-Max-Str. 3, D-81545 Munich, Germany

[21] Appl. No.: 902,368

[22] Filed: Jul. 29, 1997

Related U.S. Application Data

[63] Continuation of Ser. No. 416,851, filed as PCT/EP93/02804, Oct. 12, 1993 published as WO94/08534, Apr. 28, 1994, abandoned.

[30] Foreign Application Priority Data

Oct. 12, 1992 [DE] Germany .......................... 42 34 351.8

[51] Int. Cl.[6] ..................................................... A61F 2/32
[52] U.S. Cl. .............................................................. 623/23
[58] Field of Search ................................... 623/16, 18, 20, 623/23

[56] References Cited

U.S. PATENT DOCUMENTS 4,435,854  3/1984  Keller .

FOREIGN PATENT DOCUMENTS

| 0 222 236 A1 | 5/1987 | European Pat. Off. . |
|---|---|---|
| 0 240 815 A10 | 10/1987 | European Pat. Off. . |
| 0 477 113 A1 | 3/1992 | European Pat. Off. . |
| 2 583 286 A1 | 12/1986 | France . |
| 2 618 667 | 2/1989 | France . |
| 3829361 A1 | 8/1989 | Germany . |
| 3913874 C1 | 5/1990 | Germany . |
| WO/91/18560 | 12/1991 | WIPO . |

Primary Examiner—David J. Isabella
Attorney, Agent, or Firm—Westman, Champlin & Kelly, P.A.

[57] ABSTRACT

The invention relates to a femur stem (10) of a hip joint endoprosthesis. The cross-section of the femur stem twists from its proximal to its distal region in such a way that the transverse-oval cross-section in the proximal region turns towards the distal direction such that the cross-section is sagittal-oval in the distal region. The femur stem according to the invention can easily be introduced into the medullary canal and is optimally adapted to the shape of the medullary canal.

11 Claims, 8 Drawing Sheets

STEM OF A FEMORAL COMPONENT OF A HIP JOINT ENDOPROSTHESIS

This is a continuation of application Ser. No. 08/416,851, filed as PCT/EP93/02804 Oct. 12, 1993, published as WO94/08534 Apr. 28, 1994, now abandoned.

The invention relates to a stem or shaft of a femoral component of a hip joint prosthesis which can be implanted either cementlessly or by using bone cement, as well as to a femoral component comprising such a stem.

It is hard to imagine present-day orthopaedics and surgery concerning the locomotor system without joint replacement operations. However, the results of these operations are very different in view of whether the prosthesis component is implanted either cementlessly or by using bone cement as well as in view of the individual hospitals.

The individual results are often hardly comparable and very often hardly reproducible even in one and the same hospital. This has finally resulted in the development of a multitude of prosthesis components, which as regards the example of the hip joint and in this connection the example of the femoral component has assumed such proportions that today more than 400 different types of such components are available on the market.

One of the main reasons for this great number of different prosthesis designs is the great variation in the morphology of individual bones and also the great variation in the properties of these individual bones. The variation in the normal anatomy and physiology is even increased by the wide range of pathological changes in the bones, which finally lead to the wear of the joint as far as not an accident is the reason for the destruction of the joint.

On account of the many unsolved problems concerning the adaptation to the nature of the bones, there exist syndromes today which are summarized as the "prosthesis disease". One of the main reasons therefor is, however, that the development of a standard prosthesis, which optimally adapts itself to an as great a number as possible of physiological shapes of the proximal end of the femur without large parts of the bone having to be removed when the bony bed is adapted to the prosthesis, has not been successful up to now.

There are various tests, such as e.g. in EP-A-0 038 908 and in U.S. Pat. No. 4,435,854, in which it is described how an anatomical adaptation to the medullary cavity of the bone can be achieved and physiological curvatures can be imitated.

Tests with natural femur have, however, demonstrated that these physiological curvatures cannot be transferred to the medullary cavity physiologically without the introduction of the femoral component being hindered at the beginning, i.e. the introduction of the anatomically adapted shape into the bone is not successful without correspondingly preparing the route of access or route of implantation.

Thus, an object underlying the present invention is the provision of a femoral component of a hip joint prosthesis which is optimally adapted to the medullary cavity of the bone, in particular is optimally centred in its implanted condition, and which is easily introducible into the medullary cavity of the bone.

During the systematic studies carried out within the scope of the invention for achieving the aforementioned object, it has been found out that in the past an essential criterion has been overlooked in the development of prosthesis shafts. In the studies, a contortion or twisting of the bone on account of the very strong muscular forces applied at the outside of the bone was noticed. This scientific finding is the basis for the invention, by means of which the problem of fitting the femoral component into the bone surprisingly can be solved very simply and at low costs.

In order to achieve the aforementioned object, the invention is based on the concept that the medullary canal twists in the same way as the cylindrical tube of the bone and thus also the bone structures inside the medullary canal, namely the lattice structures of the spongiosa trabeculae. Thus, it has been found according to the invention that the medullary canal of the proximal femur can unambiguously be defined by an axis and that this axis also represents the ideal construction axis for the prosthesis itself and for the route of access of the prosthesis, i.e. the route of operation. It has additionally been found that the neck of the femur opens in a three-dimensionally inclined manner into the medullary canal of the femur and that its structures reappear inside the bone in the medullary canal of the femur shaft cylinder and thus define compartments in the cross-section of the proximal femur bone.

The cross-sections both of the medullary canal and the shaft cylinder correspond in the proximal part, i.e. at the height where the neck of the femur opens thereinto, to a transverse oval or an ellipse having its longer axis in the medial-lateral direction. In the area of the muscle origins at the lesser trochanter, the cross-sections change into a more rectangular configuration, which is maintained in the entire proximal area of the metaphysis up to the transition to the diaphysis, i.e. the actual cylindrical shaft tube of the femur. It has been found that the latter has at its beginning, i.e. proximally, a cross-section that is rather similar to a transverse oval and then gradually changes through the sections of the proximal half of the femur up to the area in which in the implanted condition the tip of the prosthesis is arranged, into a sagittal oval or an ellipse having its longer axis in the ventral-dorsal direction. By means of a three-dimensional reconstruction of these sections, a twisting of the medullary canal could be determined. According to the invention, the shape of the femur shaft is optimally adapted to this form of the medullary canal. In one embodiment, the cross-sections of the femur stem according to the invention is transverse-oval in the proximal region and "turns" towards the distal direction such that it is sagittal-oval in the distal area.

The morphology of the femur which was developed in the paper of Noble, "The anatomic basis of femoral component design", Clin. Orthop. Rel. Res. 235 (1988), 148–165, reveals that the femur has an S-shaped curve in the axial path of the rays of an X-ray image such that in the proximal region the centre of the radius of the curvature is located in front of the femur, i.e. ventrally, and in the distal region the centre of the curvature is located dorsally with respect to the femur. Accordingly, an adaptation to this S-shaped curve would be desirable in order to optimally centre a prosthesis in the femoral medullary canal.

The exact analysis within the scope of the invention surprisingly has revealed, however, that in particular in that area in which mainly force is transmitted between the bone and the prosthesis, i.e. on the dorsal side of the femoral medullary canal as well as in the medial and antero-medial region, the dorsal wall runs straight and can be defined such that the back (dorsal) wall of the neck of the femur, which appears as the isthmus of the neck in the lateral X-ray image of the femur, and the back (dorsal) wall of the femoral medullary canal form a plane parallel to which the implantation axis must be defined. In this way, a straight and linear access to the medullary cavity is defined which is also reflected in the design of the prosthesis stem according to the invention.

The invention is based on the finding that a body adapted to the medullary cavity, for instance a femur stem of a hip joint endoprosthesis, must be twisted or contorted in the same way as the medullary canal or the bone so that it can be introduced along the implantation axis without pushing against the bone. This twisting or torsion is preferably anti-clockwise from the distal to the proximal direction in the case of a left stem, and clockwise in the case of a right stem. It has turned out that upon straightening a shaft curved initially in an S-shape, said shaft sinks further into the femoral medullary canal than the originally S-shaped adapted shaft which is otherwise similarly designed. A straight shaft twisted in itself can, in contrast to an otherwise identical S-shaped shaft, be completely introduced into the medullary canal without further bone having to be removed. As regards the design of the prosthesis according to the invention, it is deduced therefrom that the latter must preferably be designed straight on the dorsal side and/or that the prosthesis body must be twisted in itself from its proximal to its distal part, namely by about 15° to 195°, preferably by about 45° to 135°, more preferably by about 90°, relative to the proximal section of the femur into which the femoral component is implanted. Hence, the torsion extends for instance along the proximal 21 cm of the femur. Even slighter torsions quite considerably facilitate the introduction of the prosthesis. Moreover, it is thus achieved that the centre of the head anatomically adjusts itself in the sense of an anteversion of the femur.

The femur stem according to the invention has preferably along its entire length, in any case in its proximal region, a concave recess or groove or a flattening, which extends helically or spirally in the longitudinal direction of the femur stem. In the proximal region of the shaft, the recess, groove or flattening (hereinafter called "recess" in short) is located on the dorsal side of the shaft and in the distal direction it turns spirally towards the lateral side of the shaft. A torsion of the femur shaft can also be defined by means of this recess.

Furthermore, the invention is based on the finding that the front (ventral) wall of the prosthesis stem—as seen in the axial, lateral path of the rays of an X-ray image—must adapt itself to the course of the neck of the femur, in the sense that the surface of the front wall must be prepared in a curved manner. In this connection, the centre of the curvature is located in front of the femur, i.e. ventrally, and the curvature has radii between about 60 and 180 mm, preferably between 80 and 150 mm, more preferably 120 to 130 mm. A parabolic course of the curvature from the distal to the proximal direction is particularly advantageous so that in this projection the bending radius continuously decreases towards the proximal direction.

In the view from the ventral or the dorsal direction, i.e. in the antero-posterior path of the rays, the shaft is curved at its medial side, the centre of the curvature being located medially with respect to the femur, and the curvature has radii between about 15 and 85 mm, preferably between 25 and 55 mm. In this case too, the curvature has preferably a parabolic course such that the bending radius decreases from the distal to the proximal direction. Bending radii of about 36 to 40 mm show preferably the optimal adaptation to the force transmission plane within which the centre of rotation is described, as shown in PCT/EP 92/01925.

In the studies underlying the invention, a very considerable retrotorsional component could be detected on account of histological evidence above all during climbing stairs and standing up from a sitting position. The surfaces transmitting forces have been thoroughly analyzed. From this analysis, a surface design of the prosthesis stem can be derived which differs at the dorsal side from the design of the ventral side. At the dorsal side, the surface is not only axially straight but its cross-section is additionally concave. At the ventral side, the cross-section of the surface is convex. The surfaces transmitting forces are mainly in the proximal area of the prosthesis. It could be shown that in the case of a cemented component a uniform cement layer thickness around the circumference of the prosthesis is surprisingly obtained by the mentioned surface design of the prosthesis. In the case of a cementless component, the surface design of the prosthesis stem according to the invention leads to a considerably larger contact area between implant and bone. Furthermore, in the case of the design of the prosthesis surface according to the invention, only very little bone must be removed prior to the implantation, for example by means of a diamond hollow grinding tool according to DE-A-32 02 193, in order to be able to anchor the prosthesis stem. This means for the patient that only very little own bone substance must be sacrificed and, if a diamond hollow grinding tool is used, that additionally this substance is also again available for bone transplants. As the head of the femoral neck is severed in a shaft implantation, and the remaining femoral neck with its very compact dorsal wall must be broken through by the prosthesis stem, this dorsal wall must be removed in the case of all straight stems which are not twisted; however, it has turned out that in the implantation of the twisted stem according to the invention, which is concave at its dorsal side, the dorsal wall remains intact.

From the cross-sections of the proximal femur, furthermore a knob-shaped distension of the proximal prosthesis stem according to the invention can be derived, which could not be observed in the conventional prostheses up to now. Put in terms of the mass of the prosthesis, it can thus be achieved that a main proportion of the mass can be concentrated in the proximal and medial region and the prosthesis can taper off towards the distal region to a greater extent than conventional prostheses. In all attempts to implant such prostheses according to the invention in the bone, an exact placement of the shaft in the centre of the medullary canal surprisingly was achieved virtually automatically, and this even without a "centralizer". On account of the fact that the implantation axis and the construction axis of the prosthesis according to the invention coincide, a drive-in hole at the proximal point of exit of the construction axis at the stem enables a reproducible implantation of the prosthesis.

In particular in the proximal area, the femur stem according to the invention can also be designed such that its cross-section has a U-shape, wherein the U-shape is open towards the lateral direction and has a broad contact by means of its curvature which is convex in the medial area. In the further course distally, the femur stem—seen horizontally—can have a transverse-oval to rectangular cross-section with clearly rounded edges.

In the femur stem according to the invention, the angle between the axis of the stem (drive-in axis) and the femoral neck axis, i.e. an axis perpendicular to the cross-section of the femur stem at its proximal end in the projection in the antero-posterior path of the rays, i.e. viewed from the ventral or the dorsal direction, is as a rule about 126° to 144°, preferably about 132° to 140°, more preferably about 135°. In the side view from the medial or lateral direction (axial path of the rays), there is also an angle formed between the axis of the stem (drive-in axis) and the femoral neck axis, which is perpendicular to the femur stem at its proximal end. This angle (antetorsion) is generally about 0° to 12°, preferably about 5° to 10°, more preferably about 8° to 9°.

In detail, the implantation of the femoral component according to the invention is carried out as follows:

First of all, the hip joint is laid bare in the usual way via a lateral access and the capsula is opened and removed. Subsequently, the femur is completely dislocated and externally rotated with a strong dislocation curette. In this position, the medullary cavity can be incised with a diamond hollow grinding tool in the prolongation of the preoperatively planned implantation axis at the medial circumference of the greater trochanter, slightly dorsally with respect to its median plane, so that the implantation route is exposed over its entire length. The bone cylinder then being removed with an extractor and consisting of compact substance and spongiosa has typically a length of only 8 to 9 cm when the free medullary cavity has already been reached. Then a cylindrical guide instrument is inserted into the implantation canal. A sawing template is slipped over the guide instrument, which sawing template opens the way for the oscillating saw exactly in the resection plane. In the next step, the pathologically changed head of the hip is severed therewith, the guide instrument is taken out again and a boring guide for the diamond hollow grinding tool is inserted. Along this boring guide, the ridge of the spongiosa at the neck of the femur can be sparingly widened in a way fitting to the selected stem of the prosthesis by cylindrical milling. The calcar femorale is retained in this way. The calcar femorale is considered to be that proportion of the femoral neck which reaches into the free medullary canal of the diaphysis shaft and is found as a compact structure in the cross-section at the height of the femoral neck and which divides the medullary cavity into a ventral and a dorsal compartment. The implantation route leads through the ventral compartment of the medullary cavity. Then again a guide instrument is inserted into the opening canal, and an external boring guide is slipped onto the femur at the preoperatively determined height, for instance between 17 and 21 cm distally from the resection surface. A bore having a diameter of 4.5 mm is placed antero-laterally here and a drainage cannula having a self-cutting thread is screwed in, as described in EP-A-305 417. Subsequently, the mandrin is removed, the medullary cavity is rinsed and sucked off. Thereafter, a second drainage cannula is screwed in the ridge of the trochanter in the direction of the linea aspera and the bone cement is prepared by vacuum mixing. While an assistant is mixing the bone cement, a test prosthesis of the selected type is inserted, controlled and subsequently removed again, a seal is placed on the femur for sealing it, the vacuum pump is turned on and the finished precompressed bone cement is sucked into the bony bed under vacuum by means of a cement press or cement syringe. It is first sucked distally and then the sucking drainage is opened proximally. At the same time, the prosthesis shaft is carefully introduced along the implantation axis and, depending on the viscosity of the bone cement, slowly positioned. After the bone cement has cured, the vacuum is shut off and projecting cement residues are removed. After a spherical head has been positioned, the femoral component is reset with the femur, wherein again a vacuum is applied both in the area of the acetabulum and in the area of the femur.

Figure 2:
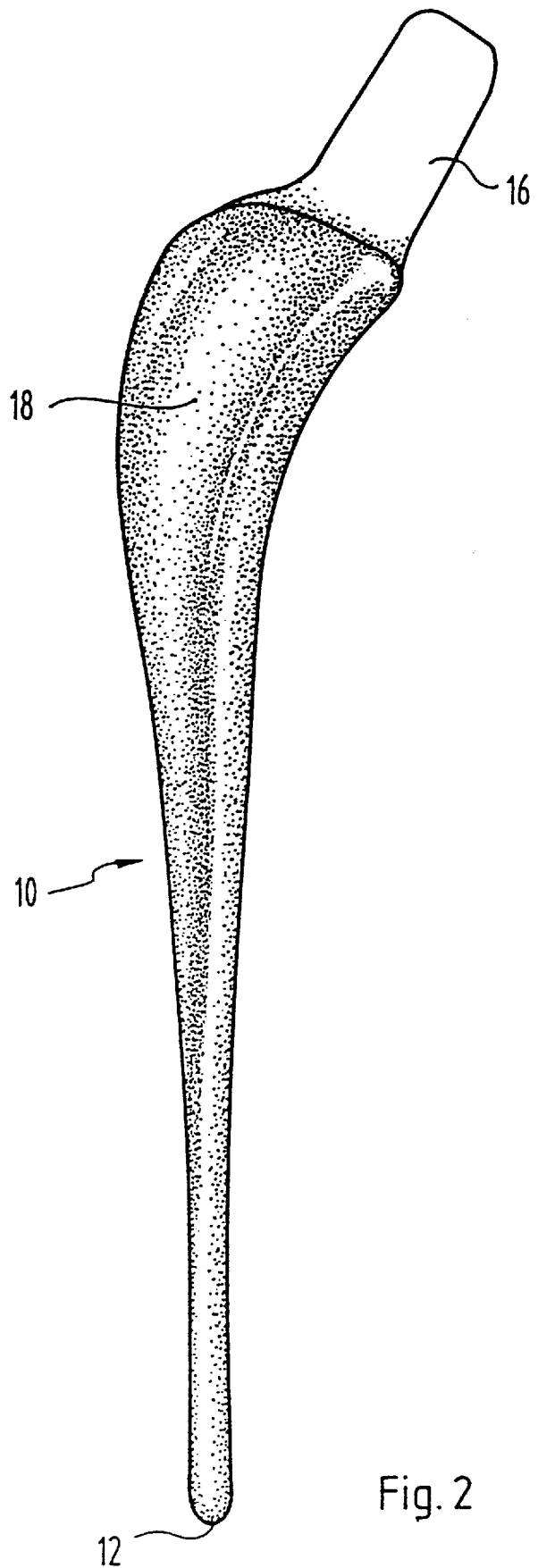
Figure 3:
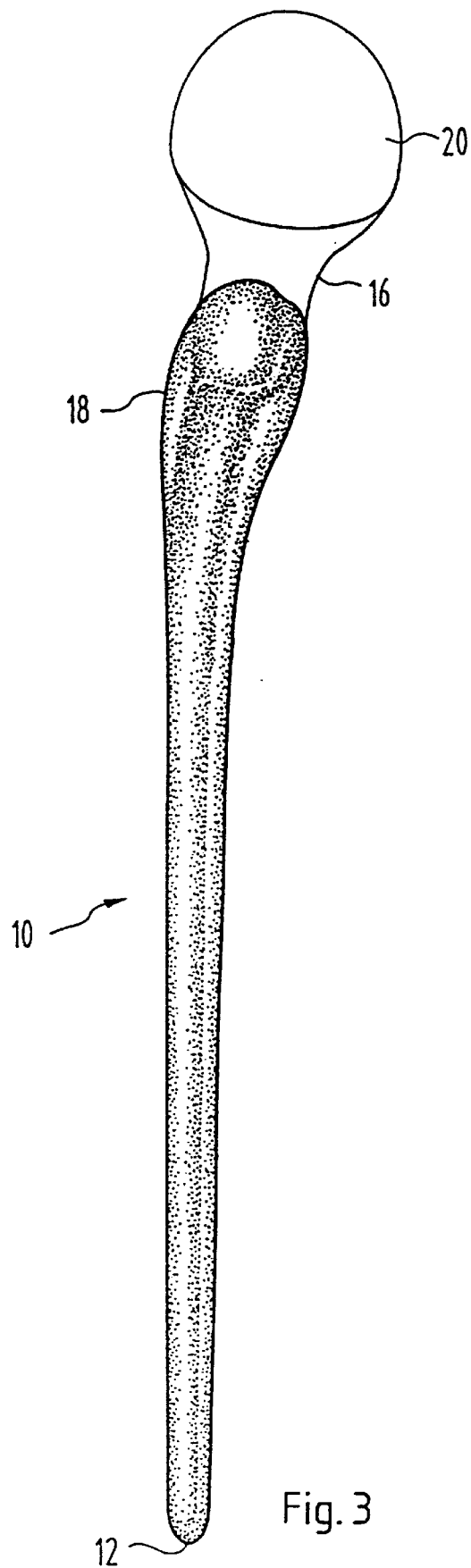
Figure 4A:
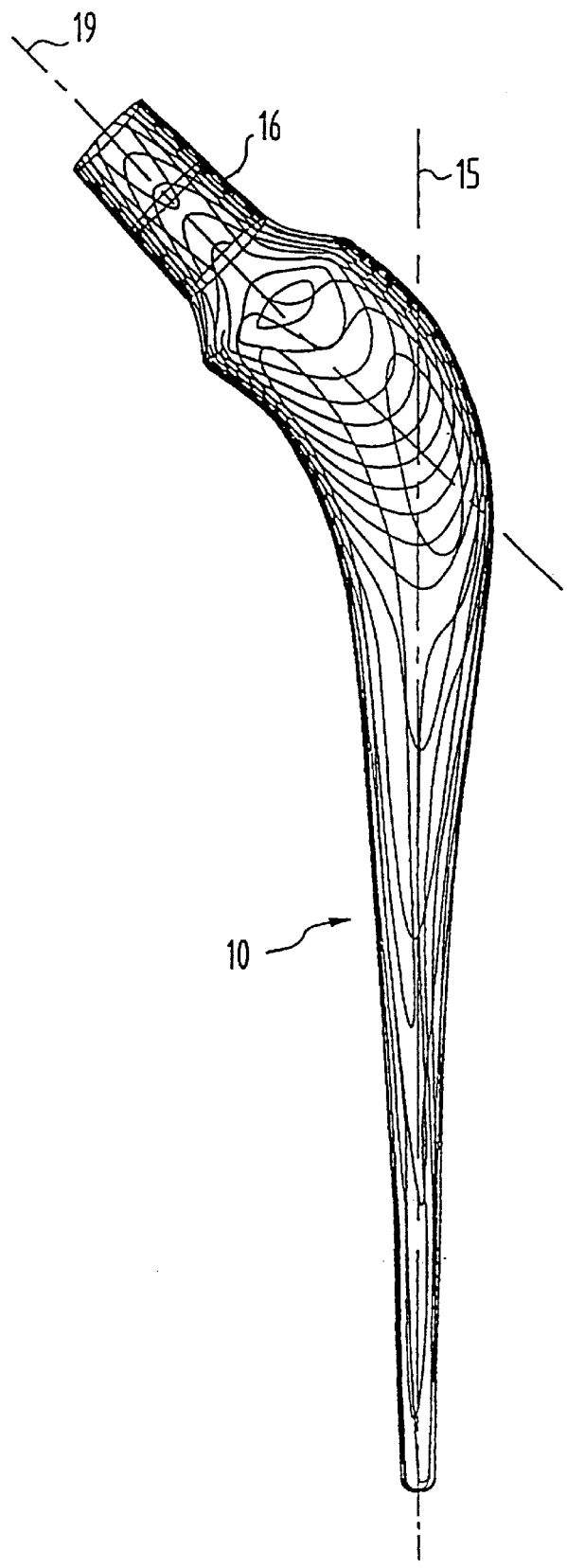
Figure 4B:
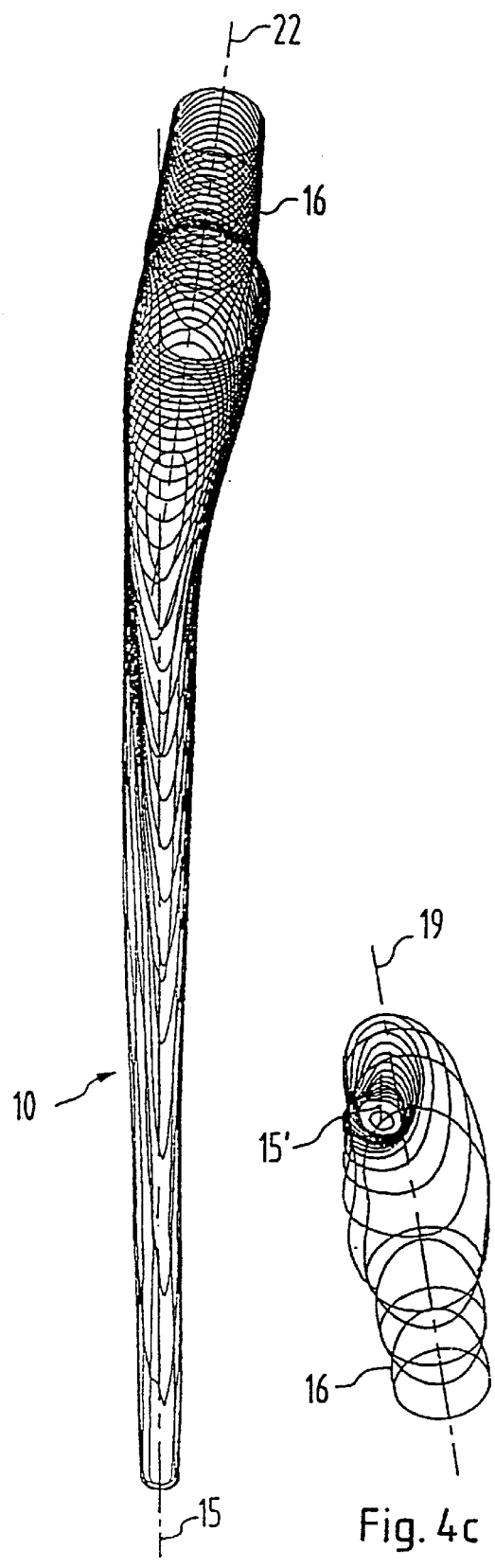
Figure 4C:
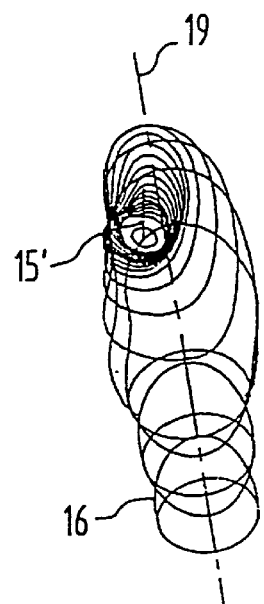
Figure 5:
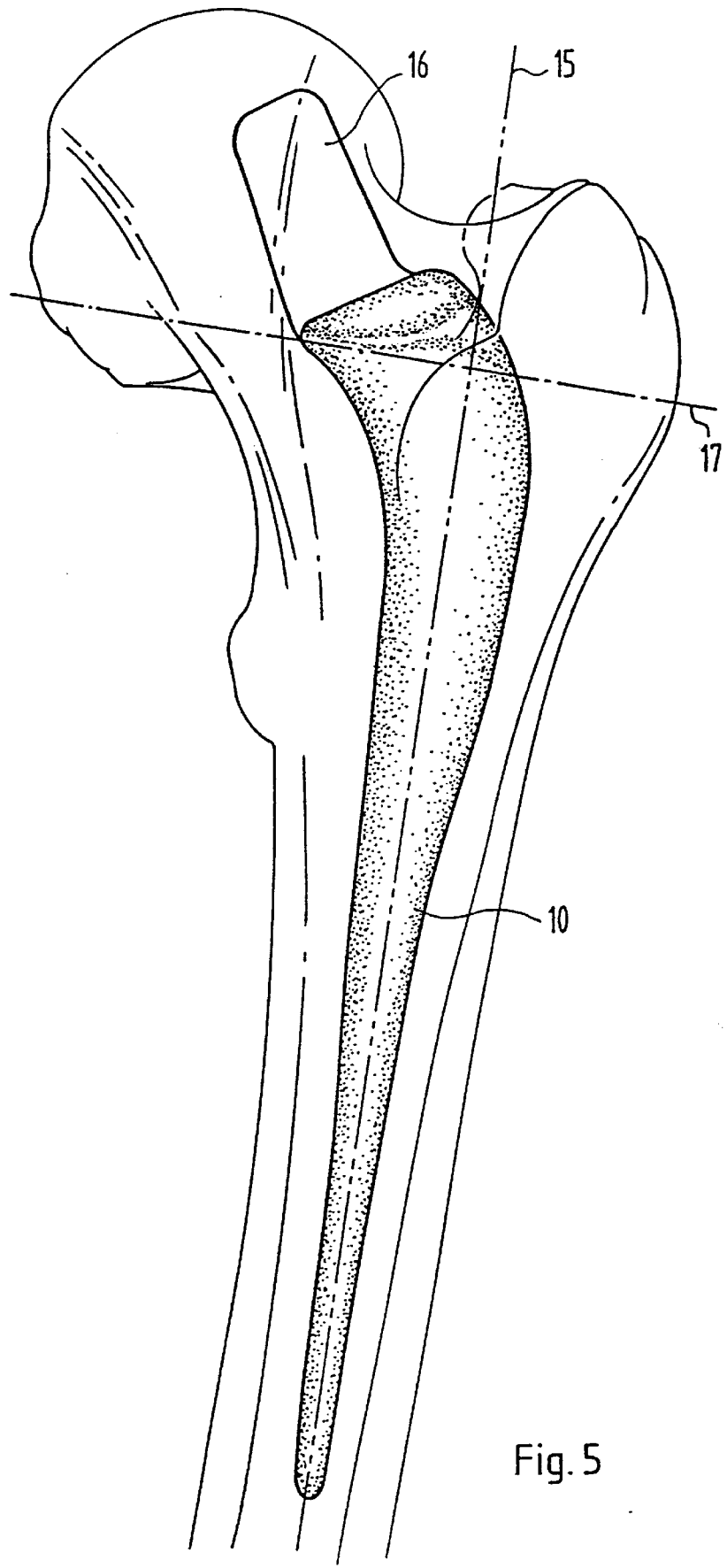
Figure 6:
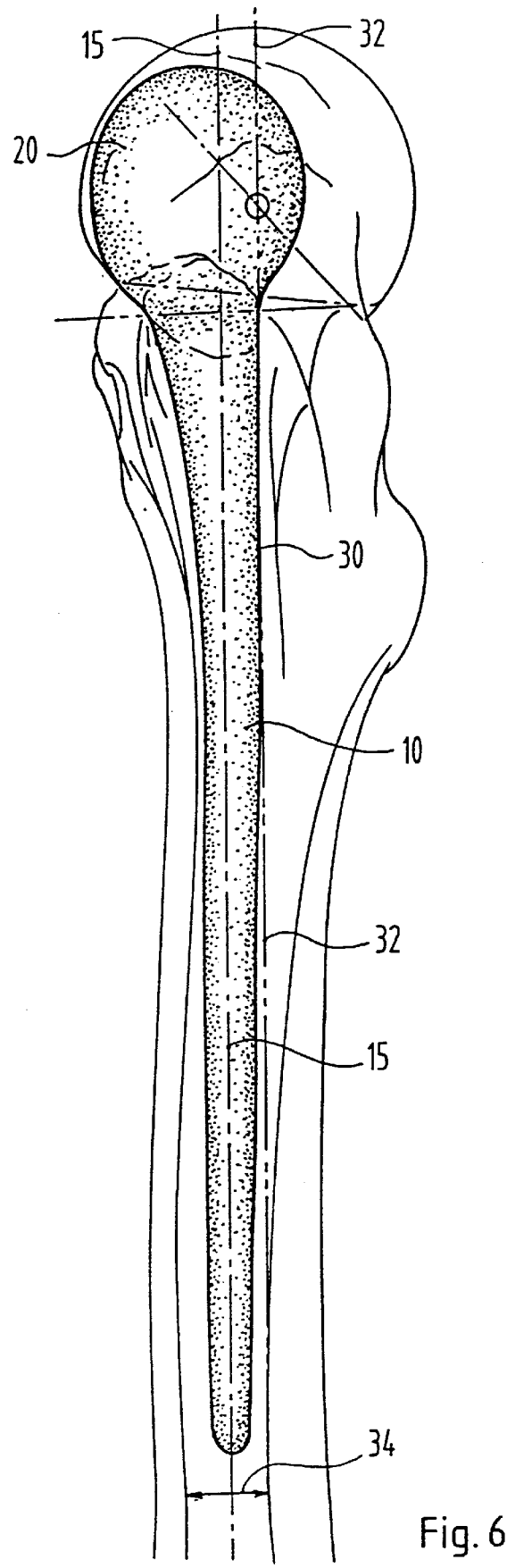
Figure 7:
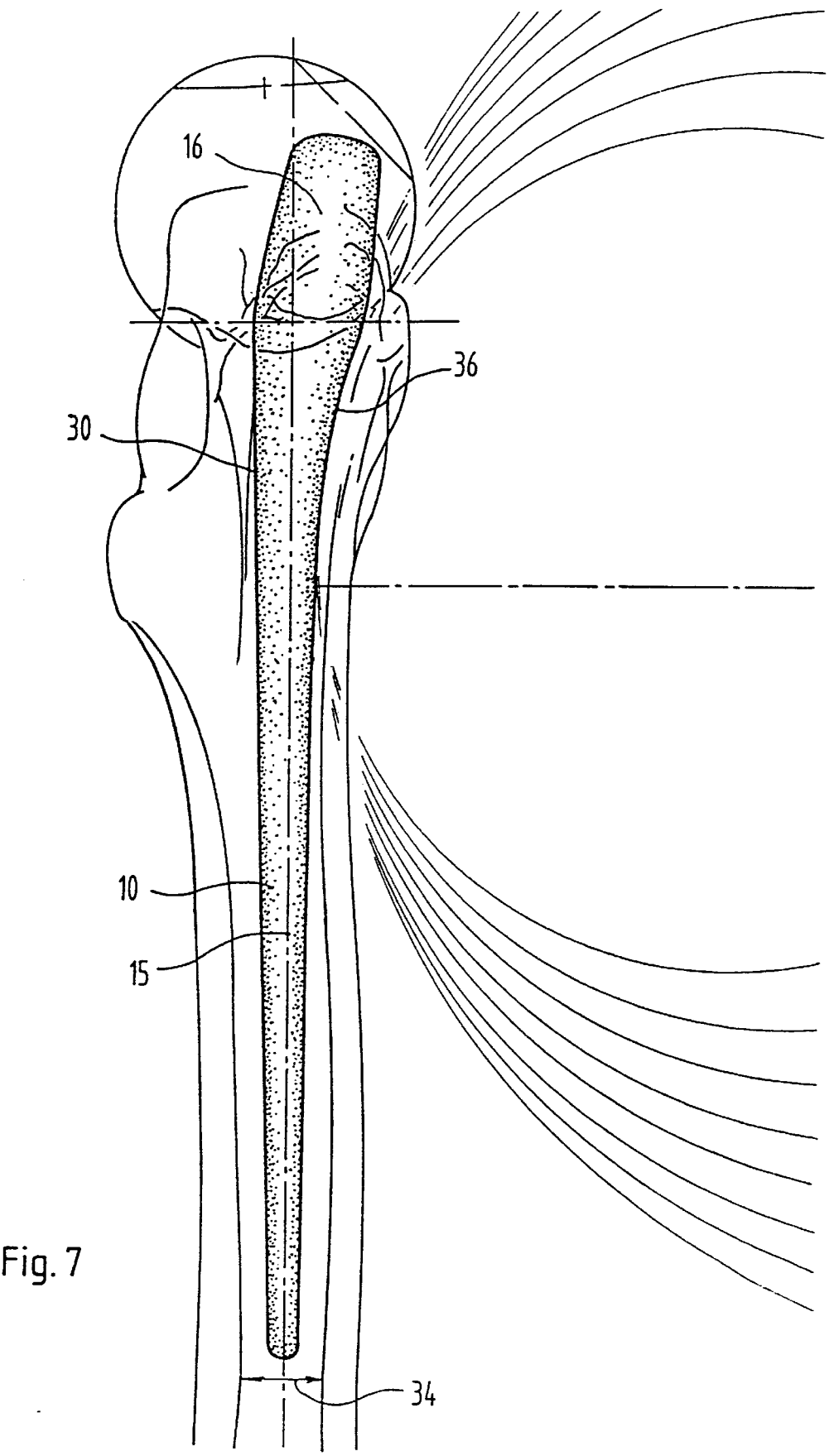
Figure 8:
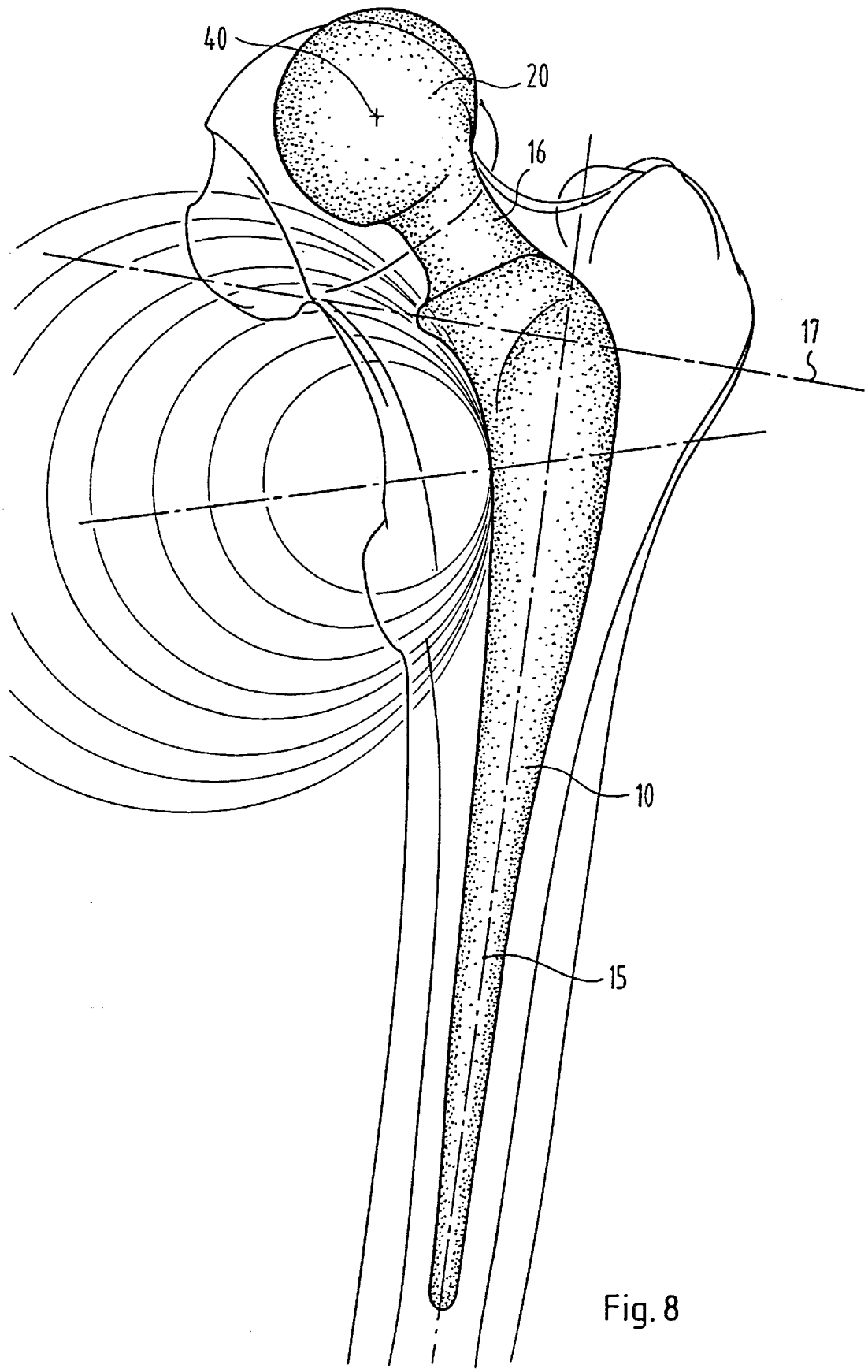

The invention will be illustrated in the following by means of the drawings, in which:

FIG. 1a shows a view of a femur stem according to the invention from the dorsal direction, FIG. 1b shows several cross-sections of the femur stem of FIG. 1a at different positions in the axial direction, FIG. 1c shows a view of a femur stem of FIG. 1a from the medial direction, FIG. 2 shows a view of an embodiment of the femur stem according to the invention (left prosthesis) from the dorsal direction, FIG. 3 shows a view of the same embodiment from the medial direction, FIGS. 4a, 4b and 4c show an embodiment of the femur stem according to the invention (left prosthesis) in a CAD representation from the front (antero-posterior path of the rays), from the lateral direction (axial path of the rays) and in a top view, FIG. 5 shows a sectional view of an embodiment of the femur stem according to the invention (antero-posterior path of the rays, view from the front), FIG. 6 shows a sectional view of an embodiment of the femur stem according to the invention with the spherical head placed on it (axial path of the rays, view from the lateral direction), FIG. 7 shows a sectional view of an embodiment of a femur stem according to the invention having a conical neck (axial path of the rays, view from the medial direction), and FIG. 8 shows a sectional view of a femur stem according to the invention (antero-posterior path of the rays, view from the front).

The Figures show embodiments of the femur stem according to the invention approximately in natural scale. All dimensions in FIG. 1 are in mm, unless indicated otherwise.

FIG. 1a shows a femur stem 10 with a prosthesis tip 12 and a neck base 14 as well as a construction axis 15. Furthermore, a concave recess 18 can be seen in FIG. 1a, which is arranged in the proximal region on the dorsal surface and continuously spirally twists or contorts to the lateral side of the prosthesis towards the distal region.

The numbers in brackets at the right side of FIG. 1a indicate the entire width of the femur stem in a sectional view in the respective axial position, the other numbers of the respective series indicate the proportion which is lateral and medial relative to the axis 15. These data provide a good basis as regards the mass distribution of the prosthesis in the lateral and medial region of the axis.

It can also be deduced from FIG. 1a that the entire length of the femur stem is about 187 mm, the diameter in the distal area is about 5.5 mm, the lateral distance between the axis 15 and the proximally highest point of the stem is about 7 mm and the angle between the axis 15 and the axis of the neck of the femur, i.e. between the axis 15 and the proximal end face of the femur stem, is about 37°.

FIG. 1b shows the shaft cross-sections in different axial positions. It is clearly recognizable that the cross-section in the proximal area is essentially transverse-oval or elliptic with the long axis in the medial-lateral direction, and has a concave recess on the dorsal side. The cross-section decreases towards the distal end and continuously "turns" so that at the distal end the long axis of the elliptic cross-section extends from the ventral to the dorsal direction and the cross-section of the implanted shaft is sagittal-ovally oriented. At the same time, the concave recess also continuously turns from the dorsal to the lateral side. The width as well as the radius of the concave recess likewise continuously decrease from the proximal to the distal end, wherein the width of the recess in the proximal area is about 20 mm and in the distal area about 3.8 mm, and the radius in the centre of the recess decreases from about 25 mm in the proximal area to about 2 mm in the distal area. The transition between the recess and the remaining wall of the prosthesis stem is rounded off, wherein in FIG. 1b, the rounding radii are indicated. Furthermore, in FIG. 1b the smallest diameter of the prosthesis cross-section is indicated, which is measured in each case approximately from the centre of the recess and decreases from about 13 mm in the proximal area to about 4.5 mm in the distal area. The cross-sectional shapes in the proximal area in a frontal plane may be reni-form (kidney-shaped) or pyriform (pear-shaped).

In the sectional view according to FIG. 1c (view from the medial side), the numbers at the left side show also the entire width of the cross-section in the respective axial position, the further series of numbers in the proximal area indicate the distribution of the cross-section on the dorsal (at the left side in FIG. 1c) and the ventral side of the axis 15. It can be deduced therefrom that in the proximal area the centre of mass of the shaft is located ventrally relative to the axis of the shaft and a curvature is formed such that the centre of the curvature is located ventrally (at the front). This is indicated in FIG. 1c by the bending radius "R". As can be derived from FIG. 1b, the curvature extends approximately along 57 mm from the proximal end of the femur stem.

FIG. 2 shows the view of a prosthesis 10 according to the invention from the dorsal side. The prosthesis comprises a conical neck 16 for placing different spherical heads thereon. In FIG. 2, the conical recess or groove 18 can clearly be recognized, which in the proximal area extends at the dorsal side and continuously turns or "twists" to the distal side in the lateral direction of the prosthesis. As can similarly be seen in the cross-sections according to FIG. 1b, the groove 18 turns from the proximal to the distal region by a total angle of about 90°.

FIG. 3 shows a femur stem 10 with a neck 16 and a fixed head 20 (standard prosthesis) in a view from the medial side (left prosthesis). The femur stem of FIG. 3 corresponds to the femur stem according to FIG. 2. The groove 18 can be recognized in the proximal area on the dorsal side of the femur stem and turns in the distal direction towards the lateral side, i.e. into the plane of projection.

FIG. 4a shows a prosthesis stem 10 according to the invention with a neck 16 (left prosthesis) in the antero-posterior path of the rays in a CAD representation. The neck 16 is aligned in the direction of the axis 19 of the femoral neck. In the prosthesis shown, the angle between the axis 15 (drive-in axis of the prosthesis) and the axis 19 of the femoral neck, which is perpendicular to the proximal cross-sectional area of the stem 10, is about 45°.

It can furthermore be derived from the representation of the prosthesis in the axial path of the rays according to FIG. 4b that the angle between the axis 15 and the axis 22 of the femoral neck is in this representation about 9° on account of the curvature of the prosthesis stem in the proximal area towards the ventral direction.

In the schematic top view of a sectional drawing of the prosthesis according to FIG. 4c, several prosthesis cross-sections are drawn in from which also the twisting of the cross-section of the stem from the proximal to the distal direction can be recognized. In FIG. 4c, the axis 19 of the femoral neck is also drawn in and the drive-in axis 15' is indicated.

FIG. 5 shows a femur stem 10 according to the invention with a conical neck 16 in the antero-posterior path of the rays (sectional view from the front, left prosthesis) in the implanted condition. The axis 15 corresponds to the median axis of the femur and the implantation axis. Furthermore, a line 17 can be recognized in FIG. 5, along which the head part can optionally be displaced, as described e.g. in PCT/EP 92/01925.

FIG. 6 shows a femur stem 10 with a head 20 in the implanted condition in a view from the lateral side (axial path of the rays). In addition to the axis 15, which corresponds to the construction axis of the prosthesis or the implantation axis, and to the median axis of the femur, a tangent 32 is drawn into FIG. 6, which in the axial path of rays touches the dorsal wall of the neck of the femur and the dorsal wall of the femoral medullary canal. The axis 15 and the tangent 32 extend essentially parallel, the deviation should be no greater than ±5%, preferably no greater than ±3%. In FIG. 6, reference sign 34 designates the isthmus, i.e. the narrowest spot of the medullary canal.

FIG. 7 shows similarly to FIG. 6 a femur stem 10 according to the invention with a conical neck 16 in the axial path of the rays (viewed from the medial side). In particular the straight course of the dorsal side 30 of the stem in the proximal area and the curvature of the ventral side 36 in the proximal area are illustrated in FIG. 7. Several bending radii have, as examples, been constructed at the ventral side, which are preferably between 80 and 150 mm. In this connection, the centre of the curvature is located ventrally. The curvature in the proximal area has a parabolic course and the bending radius decreases substantially continuously from the distal towards the proximal end.

FIG. 8 shows a femur stem 10 comprising a neck 16 and a fixed head 20 in a similar view to that in FIG. 5 (standard prosthesis). Reference sign 40 designates the centre of rotation. It can be deduced from FIG. 8 that the prosthesis is centrally anchored in the femoral medullary canal. FIG. 8 also shows the curvature of the shaft in the proximal area on the medial side, wherein in FIG. 8 several bending radii are exemplarily indicated, which preferably are between 25 and 55 mm, more preferably between 36 and 40 mm. The curvature has a parabolic course and the bending radius decreases in the proximal area substantially from the distal to the proximal end.

I claim:

1. A femur stem having a proximal end and a distal end of a hip joint endoprosthesis whose cross section in a proximal area in the frontal plane is selected to be one of the cross sectional shapes consisting of reniform or pyriform, and having a curved concave surface on a dorsal side at the proximal area, the concave surface being twisted along a length of the stem toward the distal end such that the concave surface on the dorsal side in the proximal area turns to a lateral wall of a medullary canal in which the stem is inserted in direction toward the distal end, each cross section along the stem to the outer end having a convex circumference at locations other than the concave surface side, a central axis of the stem in the proximal area being angulated in a frontal and axial plane.

2. The femur stem according to claim 1, wherein the twist of the concave surface is substantially between 15° to 195°, about said central axis extending from the proximal end to the distal end.

3. The femur stem according to claim 1, further comprising a neck portion having a conical region for receipt of a ball joint head.

4. The femur stem of claim 1 wherein the central axis of the stem in the proximal area is curved in a radius between 60 and 180 mm to form the angulation.

5. The femur stem according to claim 1 wherein the central axis of the stem in the proximal area has a radius of curvature which continuously decreases from a distal end of the curve towards the proximal end of the stem.

6. The femur stem of claim 1 wherein the central axis of the stem in the proximal area is angulated in a parabolic curve.

7. A femur stem of a hip joint endoprosthesis, having a longitudinal axis and a cross-section that is generally rounded and forming dorsal, ventral, lateral and medial sides, a portion of the femur stem having a surface portion selected from a group consisting of a flat surface and a concave surface and extending generally parallel to the longitudinal axis, and the surface portion being located on the dorsal side of the femur stem in a proximal region and twisting to the lateral side in a direction towards a distal end forming a prosthesis tip in the range of 80° to 100° about the longitudinal axis.

8. A femur stem of a hip joint endoprosthesis according to claim 7, wherein the ventral side of the femur stem when viewed from the medial side of the stem is formed in a curve about a center axis extending transverse of the longitudinal axis and on a ventral side of the stem, the curve being along a portion of the stem no more than one-third of the length of the stem from a proximal end of the stem.

9. The femur stem according to claim 8, wherein the dorsal side of the stem in the proximal one-third of the stem, forms a substantially straight surface.

10. The femur stem according to claim 8, wherein the curve about the center axis of the stem has a radius between 60 and 180 mm.

11. The femur stem according to claim 8, wherein the curve has a radius of curvature which continuously decreases from a distal end of the curve towards the proximal end of the stem.

* * * * *